(12) United States Patent
Boday et al.

(10) Patent No.: US 9,631,119 B1
(45) Date of Patent: Apr. 25, 2017

(54) POLYTHIOAMINAL DISPERSIONS AND COATINGS

(71) Applicant: International Business Machines Corporation, Armonk, NY (US)

(72) Inventors: Dylan J. Boday, Austin, TX (US); Jeannette M. Garcia, San Leandro, CA (US); James Lupton Hedrick, Pleasanton, CA (US); Rudy J. Wojtecki, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/952,488

(22) Filed: Nov. 25, 2015

(51) Int. Cl.
    *C04B 28/36*   (2006.01)
    *C09D 181/02*   (2006.01)
    *A01N 25/34*   (2006.01)
    *C09D 5/14*   (2006.01)

(52) U.S. Cl.
    CPC ........... *C09D 181/02* (2013.01); *A01N 25/34* (2013.01); *C09D 5/14* (2013.01)

(58) Field of Classification Search
    None
    See application file for complete search history.

(56) References Cited

U.S. PATENT DOCUMENTS

| | | |
|---|---|---|
| 5,336,807 A | 8/1994 | Burgoyne, Jr. et al. |
| 5,360,876 A | 11/1994 | Burgoyne, Jr. et al. |
| 5,840,823 A | 11/1998 | Licht et al. |
| 7,045,579 B2 | 5/2006 | Van Den Berg et al. |
| 2006/0275337 A1 | 12/2006 | Cohen Stuart et al. |
| 2015/0141293 A1 | 5/2015 | Williges et al. |

FOREIGN PATENT DOCUMENTS

| | | | |
|---|---|---|---|
| CN | 103101899 A | 5/2013 | |
| CN | 103483486 A | 1/2014 | |
| EP | 0473542 | * 8/1991 | ........... C07C 323/25 |

OTHER PUBLICATIONS

Wojtecki et al. "Developments in Dynamic Covalent Chemistries from the Reaction of Thiols with Hexahydrotriazines" J. Am. Chem. Soc. 2015, 137 (45) 14248-14251 (available online on Oct. 27, 2015).*

* cited by examiner

*Primary Examiner* — Robert S Walters, Jr.

(74) *Attorney, Agent, or Firm* — Patterson + Sheridan, LLP

(57) ABSTRACT

Methods of forming and using a polymer dispersion are described herein. The polymer dispersion includes a plurality of polythioaminal microparticles in a fluid medium that does not dissolve the plurality of polythioaminal microparticles. The fluid medium may be aqueous, for example water. The polymer dispersion may be applied to a substrate, and the fluid medium removed, to form an article substantially made of a polymerized polythioaminal mass. The dispersion, and any article made from the dispersion, may include pigments and active ingredients, such as biocides.

20 Claims, No Drawings

POLYTHIOAMINAL DISPERSIONS AND COATINGS

FIELD

The present invention relates to methods of making liquid dispersions of polythioaminal particles, and coatings made from such dispersions.

BACKGROUND

A latex is a stable dispersion of polymer microparticles in a liquid medium, which is usually an aqueous medium. Various polymers are conventionally applied via a latex to form a coating or an adhesive layer. The polymer is dispersed in the liquid medium, stabilizers such as surfactants are added to stabilize the dispersion. If a coating is desired, the mixture is applied to an article to be coated, and the liquid is evaporated to leave a polymer coating. If an adhesive is desired, the mixture is applied to one article to be adhered to form an adhesive layer, a second article to be adhered is contacted with the adhesive layer, and the articles are held in place while the adhesive dries. Most polymers used in this way are rubbers such as natural rubber, but a latex may generally be used to perform emulsion polymerization of, for example styrene to make polystyrene or styrene and butadiene to make synthetic rubber. Polymers applied in this fashion typically have limited uses. There is a need to broaden the applicability of latex methods to polymers having more uses.

SUMMARY

Methods of forming and using a polymer dispersion are described herein. The polymer dispersion includes a plurality of polythioaminal microparticles in a fluid medium that does not dissolve the plurality of polythioaminal microparticles. The fluid medium may be aqueous, for example water. The polymer dispersion may be applied to a substrate, and the fluid medium removed, to form an article substantially made of a polymerized polythioaminal mass. The dispersion, and any article made from the dispersion, may include pigments and active ingredients, such as biocides.

DETAILED DESCRIPTION

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Similarly, the terms "further comprises," "may further comprise," and "further comprising," when used in this specification, specify the presence of additional features or components, without precluding the presence or addition of other features or components. The terms "further comprises," "may further comprise", and "further comprising" in this specification do not mean that any features or components are excluded from any embodiments. When a range is used to express a possible value using two numerical limits a and b (e.g., a concentration of a ppm to b ppm), unless otherwise stated the value can be a, b, or any number between a and b.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

Polythioaminal polymers may be used to form articles by dispersing a plurality of polythioaminal microparticles in a fluid medium that does not dissolve the plurality of polythioaminal microparticles, applying the dispersion to a substrate, and removing the fluid medium to form a solid article. The solid article thus formed comprises a solid mass comprising a polythioaminal polymer.

Polythioaminal (PTA) polymers are polymers having a C—N—C—S—R—S repeating unit or an S—R—S—C—N—R'—N—C repeating unit, where R is an organic or hetero-organic group. The polymers are generally thiol-terminated, so a typical PTA molecule may have either of two general structures:

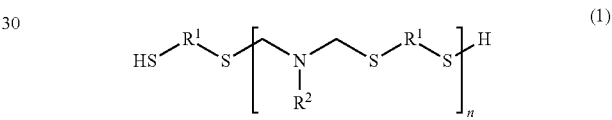

(1)

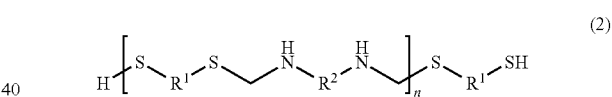

(2)

Structure (1) is formed by reacting a substituted hexahydrotriazine small molecule with a dithiol, as follows:

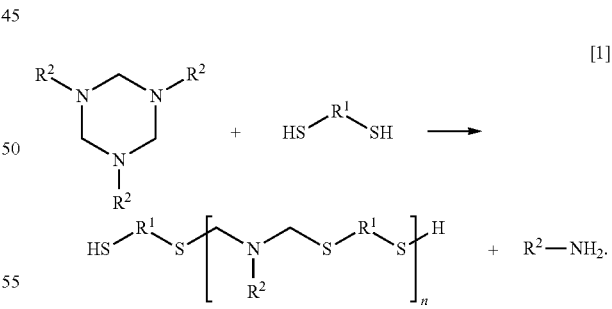

[1]

The byproduct amine must be removed from the reaction to drive growth in molecular weight of the PTA. This can be done by volatilizing the amine up to a temperature not more than about 200° C., or if the amine is not volatile at such temperatures, by including an amine scavenger, such as a cyclic carbonate or anhydride, in the reaction mixture. It is helpful in some embodiments for the amine scavenger to be orthogonal to the other reaction species (hexahydrotriazines and thiols). Propylene carbonate and succinic anhydride are two useful examples of amine scavengers that may be used.

Structure (2) is formed by reacting a primary diamine and a primary dithiol together in the presence of paraformaldehyde, as follows:

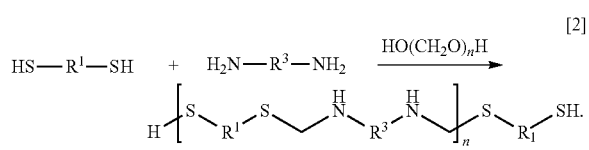

[2]

In reaction [2], $R^3$ is an organic or hetero-organic group that is electron deficient. Thus, $R^3$ may include aryl groups, $CF_3$, $NO_2$, and the like. The electron-withdrawing activity of the $R^3$ group forms a stable imine intermediate <C=N—$R^3$—N=C> with paraformaldehyde that then reacts with the dithiol to form the PTA. $R^1$, $R^2$, and $R^3$ can be functional and/or oligomeric/polymeric to impart useful additional properties to the PTA.

Reactions [1] and [2] above may be performed in solvent, or using the precursors as solvent. Polar aprotic solvents such as N-methylpyrrolidone are useful for performing reactions [1] and [2] above. The reactions are typically performed under slight heating, for example at 50° C. to 80° C., and growth of molecular weight thickens the reaction mixture. The polymer may be recovered by volatilizing residual solvent and monomer, usually under vacuum to avoid approaching degradation temperatures of the polymer. Upon recovery, the polymer may be reduced to a powder of microparticles either by direct precipitation or by mechanical processing.

PTA microparticles recovered by a process as described above can be used to form articles and coatings using a latex-style process. A plurality of PTA microparticles are dispersed in a fluid medium that does not dissolve the plurality of PTA microparticles. The PTA material may be weakly soluble in the fluid medium, so some particles may dissolve to form a very low concentration solution in the fluid medium, but the majority of the particles remain suspended in the fluid medium. In some cases the fluid medium may be aqueous. In some cases the fluid medium may be water. The PTA microparticle suspension is generally applied to a substrate, which may be a surface or a mold, and the fluid medium is removed. As the fluid medium evaporates, the PTA microparticles undergo emulsion polymerization to form covalent bonds between the microparticles such that a solid mass, which may be a coating or solid article, is formed. The solid mass mostly consists of PTA molecules crosslinked together in a polymer network.

Suspension of the PTA microparticles in the fluid medium may be aided by use of solvents and surfactants to manage electrostatic interaction between the PTA microparticles and the fluid molecules. For example, hydrophobic PTA materials, such as mainly hydrocarbon-based PTA materials, may be dispersed in water using an ionic surfactant such as sodium dodecyl sulfate to form micelles. In other embodiments, the PTA may be fully dissolved in a good solvent, and then a poor solvent may be added up to the cloud point of the mixture. Thus, in one embodiment, one of the reactions [1] and [2] may be performed in a solvent up to a desired molecular weight, and then a second fluid that is a poor solvent may be added to form PTA micelles.

A second approach to generating microparticles uses cross-linking. A multi-functional thiol precursor of the form $R^4(SH)_n$, where n is three or more, may be added to dithiol and diamine or triazine precursors in a dilute solution. Such a multi-functional thiol cross-linker may be used with either reaction [1] or [2] above to provide cross-links between polymer chains, as follows:

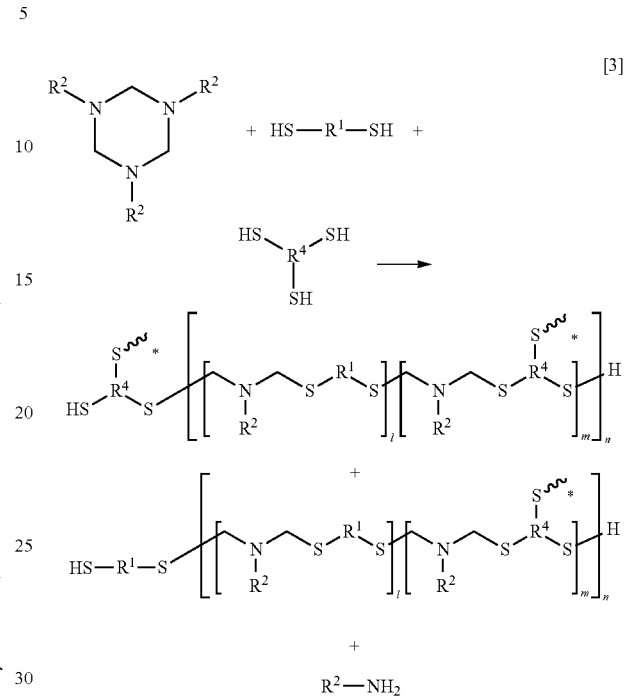

[3]

The cross-linked polymer product has the following structures:

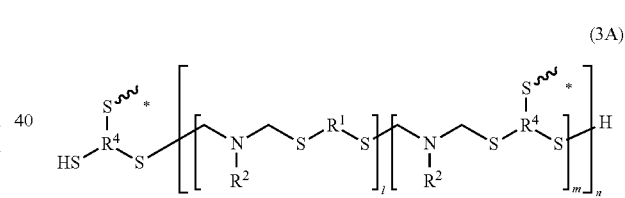

(3A)

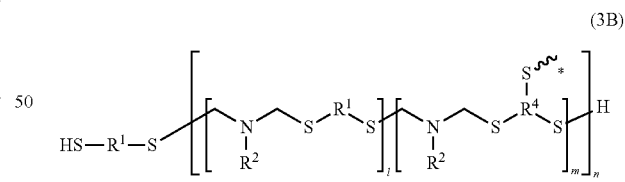

(3B)

where $R^4$ in this case is trivalent, but could have valence effectively up to 6. $R^4$ may be an organic or hetero-organic group capable of accepting multiple thiol functionalizations. Note that individual polymer molecules may have end groups formed from the dithiol, shown in structure (3B), or from the multi-thiol, shown in structure (3A). In each case, some repeating units are formed from the trithiol species, providing cross-links to other polymer chains, as denoted by wavy bonds to the sulfur atoms.

The polymer of structures (3A) and (3B) may be precipitated from solution by mixing with a miscible material that is a poor solvent for the polymer molecules. In some cases, water may precipitate the polymer. The powder thus obtained, consisting of cross-linked polymer microparticles may be dispersed in a fluid medium and applied to a substrate to form an article of applied microparticles. If the cross-linked particles do not form micelles, the PTA dispersion may be dried to form a microparticle article, and then heated to form a solid article. The applied microparticles may be heated to a temperature of 50° C. to 150° C. to form a uniform, continuously polymerized, solid article, which may be a coating.

The suspended PTA microparticles are applied to a substrate, as described above, and dried to form an article. If the microparticles do not form micelles, as may be the case with particles of cross-linked polymer, the PTA dispersion may be dried to form a microparticle article, and then heated to form a solid article. In the cross-linked case, the applied microparticles may be heated to a temperature of 50° C. to 150° C. to form a uniform, continuously polymerized, solid article. The article may be a coating or a three-dimensional molded article. Other ingredients may be added to the PTA suspension for various desired effects. The additives may be dispersed in the fluid medium before or after dispersing the PTA microparticles. For example, in one embodiment a PTA suspension may be formed as follows: 1) add a surfactant to a fluid medium; 2) disperse PTA microparticles in the fluid medium; 3) disperse additives in the fluid medium. In another embodiment a PTA suspension may be formed as follows: 1) add a surfactant to a fluid medium; 2) disperse additives in the fluid medium; 3) disperse PTA microparticles in the fluid medium.

The additives may include pigments, texturizing materials, visual effect materials, active ingredients, physical property modifiers, and other polymers. The active ingredients may include reactive species, flame retardant species, magnetic species, electrically conductive species, and bioactive species. Texturizing materials may include mineral or vegetal material such as mica, silica, bitumen, or cellulose. Flame retardant species may include phosphates, gypsum, perlite, and the like. Magnetic species may include iron particles and rare earth powders. Bioactive species may include fungicides, algicides, and bactericides such as hydantoins and isothiazolinones. Visual effect materials may include light-emitting materials such as phosphors and electroluminescent materials.

The additives may include components miscible with the fluid medium. Such additives may incorporate into the PTA article as the fluid medium is evaporated. Some such additives may be reactive with the PTA medium. For example, thiol-reactive or amine-reactive materials may be included in the fluid medium to react with residual thiol and amine sites in the PTA polymer that forms as the mixture dries. Thiol-terminated molecules may react with residual reactive thiol or amine sites of the PTA to add functionality to the article. Epoxide molecules may react with residual reactive amine sites in the PTA. If such molecules are difunctional, branching and cross-linking may be performed. For example, a di-epoxide may be included with the PTA to activate a cross-linking reaction between the amine sites of adjacent PTA chains.

The additives may also be non-reactive, and may remain in the PTA article after the fluid medium is removed by simple coalescence. In some cases, intermolecular electrostatic forces may intermediate the affinity of additives for the PTA polymer. The additives may be functionalized in some cases, for example by adding or including electron-rich groups in the molecular structure of the additive to provide an affinity for residual amine or thiol protons of the PTA.

In such embodiments, it will be most useful if the thiol- or amine-reactive additives are less volatile than the fluid medium. In some embodiments, a desired functionality may be provided in a molecule having molecular weight selected to limit volatility of the additive. For example, a low molecular weight polymer or oligomer may be functionalized with the desired functionality and then dissolved in the fluid medium with the suspended PTA particles. As the fluid medium evaporates, the PTA chains react to form the solid article, and the functionalized additive molecules remain in the PTA matrix either interpenetrating with the PTA matrix or bonded to the PTA matrix in some way (e.g. covalently, ionically, or by Van der Walls electrostatic attachment such as hydrogen bonds).

In some embodiments, a coating or article may be made by a latex process, as described herein, including more than one application and drying cycle. In a coating process, a first PTA/fluid medium mixture may be applied to a substrate and dried to form a first coating, and then a second PTA/fluid medium mixture may be applied to the substrate and dried to form a second coating. The second PTA/fluid medium mixture may overlap partially or completely with the first coating to form regions of a layered coating. In such embodiments, the first and second coatings may be the same material, or different materials, and the first and second coatings may co-adhere through chemical bonding, for example by covalent bonding of PTA molecules from the second coating with PTA molecules from the first coating, or through interfacial processes such as solution welding, in which PTA particles of the second PTA/fluid medium mixture interpenetrate with the PTA matrix of the first coating. Either the first or second coatings may contain additives that promote development of a desired interface between the coatings. For example, an adhesive such as polyisobutylene, polyisoprene, or polycyclopentadiene may be dissolved or suspended in the second PTA/fluid mixture medium to promote adhesion. Alternately, an adhesive layer may be applied covering, at least in part, the first coating prior to applying the second coating.

Any number of such coatings may be applied to achieve a desired result. Each coating may be the same material as the previous coating, or a different material. For example, the first coating may be a PTA-based material that includes a PTA of structure (1) above and the second coating may be a PTA-base material that includes the same, or a different, PTA of structure (1) above. Likewise, the first coating may be a PTA-based material including a PTA of structure (1) above, while the second coating is a PTA-based material including a PTA of structure (2) above. The first coating may include a second polymer, while the second coating includes no second polymer, or the second coating includes a second polymer different from the second polymer of the first coating. Either the first coating or the second coating, or both, or any subsequent coating, may be applied according to a desired pattern so that portions of the first coating may be exposed through the second coating to any desired degree.

The first coating and the second coating may be selected to provide desired processing characteristics. For example, the first coating may have a first susceptibility and the second coating may have a second susceptibility. If the first coating is blanket-deposited, and the second coating is pattern-deposited to expose portions of the first coating, a process may then be performed to selectively process the first or second coating depending on the different susceptibilities of the two coatings. For example, if the first coating includes a PTA of structure (1) above, and the second coating includes a PTA of structure (2) above, the substrate may subsequently be treated to apply an epoxide material to react selectively with the residual reactive amine sites of the PTA in the second coating while having no effect on the first coating. In this, way coatings can be combined and patterned to produce articles having a great diversity of surface features.

In some embodiments, an article made be molded using a latex process, as described above, and then coating using a similar latex process with a similar PTA-based material or a different PTA-based material. The embodiments described above with respect to two or more coatings may also apply when an article is molded and then coated. A first PTA/fluid medium mixture is introduced into a mold and allowed to dry and polymerize. The article thus formed is unmolded and treated in any desired way, for example shaped or textured, and then a second PTA/fluid medium mixture is applied to the article and allowed to dry and polymerize. The PTA microparticles in the second PTA/fluid medium mixture react with PTA molecules in the surface of the article, forming covalent bonds between the coating material and the coated article.

Articles made according to the latex type processes described above may be repaired by applying heat. PTA polymers undergo exchange reactions when heated. A damaged area of a PTA article, such as a coating, may be heated to activate an exchange reaction where PTA polymer chains grow together to repair the damaged area. Localized heating to 100° C. or higher is usually sufficient to activate the exchange reaction.

While the foregoing is directed to embodiments of the present invention, other and further embodiments of the invention may be devised without departing from the basic scope thereof, and the scope thereof is determined by the claims that follow.

What is claimed is:

1. A polymer dispersion, comprising:
a plurality of poly(thioaminal) microparticles; and
a fluid medium that does not dissolve the plurality of poly(thioaminal) microparticles.

2. The polymer dispersion of claim 1, wherein the fluid medium is aqueous.

3. The polymer dispersion of claim 1, further comprising a surfactant.

4. The polymer dispersion of claim 1, further comprising a pigment.

5. The polymer dispersion of claim 1, further comprising a surfactant and a pigment, wherein the fluid medium is aqueous.

6. The polymer dispersion of claim 5, further comprising an active ingredient.

7. The polymer dispersion of claim 6, wherein the active ingredient is a biocide.

8. The polymer dispersion of claim 1, wherein the plurality of poly(thioaminal) microparticles constitutes at least 50 wt % of the polymer dispersion.

9. The polymer dispersion of claim 1, wherein the plurality of poly(thioaminal) microparticles comprises polymer molecules having S—C—N—R—N—C repeating units wherein R is an organic or hetero-organic group.

10. The polymer dispersion of claim 1, wherein the fluid medium comprises a thiol-reactive material.

11. A polymer dispersion, comprising:
a plurality of poly(thioaminal) microparticles;
a surfactant; and
an aqueous fluid medium that does not dissolve the plurality of poly(thioaminal) microparticles.

12. The polymer dispersion of claim 11, wherein the plurality of poly(thioaminal) microparticles comprises polymer molecules having S—C—N—R—N—C repeating units wherein R is an organic or hetero-organic group.

13. The polymer dispersion of claim 12, further comprising an active ingredient.

14. The polymer dispersion of claim 13, wherein the active ingredient is a biocide.

15. The polymer dispersion of claim 12, wherein the plurality of poly(thioaminal) microparticles constitutes at least 50 wt % of the polymer dispersion.

16. The polymer dispersion of claim 11, wherein the aqueous fluid medium comprises a thiol-reactive material.

17. The polymer dispersion of claim 11, further comprising a pigment and a biocide, wherein the plurality of poly(thioaminal)-microparticles constitutes at least 50 wt % of the polymer dispersion, the aqueous fluid medium comprises water and a thiol-reactive material.

18. A polymer dispersion, comprising:
a plurality of poly(thioaminal) microparticles;
a surfactant;
an active ingredient;
a pigment; and
an aqueous fluid medium comprising water and a thiol-reactive material that does not dissolve the plurality of poly(thioaminal) microparticles.

19. The polymer dispersion of claim 18, further comprising an adhesive.

20. The polymer dispersion of claim 18, wherein the surfactant is an ionic surfactant.

* * * * *